(12) United States Patent
Fordenbacher et al.

(10) Patent No.: US 6,395,025 B1
(45) Date of Patent: May 28, 2002

(54) MECHANICAL HEART VALVE PROSTHESIS

(75) Inventors: Paul J. Fordenbacher, Minneapolis; Avrom M. Brendzel, Roseville; A. Tanya Shipkowitz, St. Paul, all of MN (US); Stephen A. Petersen, Lincoln, RI (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 09/224,149

(22) Filed: Dec. 31, 1998

(51) Int. Cl.[7] .................................................. A61F 2/06
(52) U.S. Cl. ...................................................... 623/2.28
(58) Field of Search ............................... 623/2.21, 2.22, 623/2.26, 2.27, 2.28, 2.29, 2.3, 2.31, 2.32, 2.33, 2.34, 2.2

(56) References Cited

U.S. PATENT DOCUMENTS

| | | | |
|---|---|---|---|
| 3,828,787 A | 8/1974 | Anderson et al. | 128/303 |
| 3,860,005 A | 1/1975 | Anderson et al. | 128/303 |
| 4,078,268 A | 3/1978 | Possis | 3/1.5 |
| 4,178,639 A | 12/1979 | Bokros | 3/1.5 |
| 4,306,319 A | 12/1981 | Kaster | 3/1.5 |
| RE31,040 E | 9/1982 | Possis | 3/1.5 |
| 4,416,029 A | 11/1983 | Kaster | 3/1.5 |
| 4,443,894 A | 4/1984 | Klawitter | 3/1.5 |
| 4,532,659 A | 8/1985 | Kaster | 623/2 |
| 4,863,458 A | 9/1989 | Bokros | 623/2 |
| 5,061,278 A | * 10/1991 | Bicer | |
| 5,178,632 A | 1/1993 | Hanson | 623/2 |
| 5,397,347 A | 3/1995 | Cuilleron et al. | 623/3 |
| 5,607,469 A | 3/1997 | Frey | 623/3 |
| 5,824,062 A | 10/1998 | Patke et al. | 623/2 |

FOREIGN PATENT DOCUMENTS

| | | |
|---|---|---|
| EP | 0 289 404 A2 | 11/1988 |
| WO | WO 96/29957 | 10/1996 |

* cited by examiner

*Primary Examiner*—Bruce Snow
(74) *Attorney, Agent, or Firm*—Hallie A. Finucane, Esq.; Westman, Champlin & Kelly, P.A.

(57) ABSTRACT

Mechanical heart valve prostheses are disclosed that inherently reduce the probability of thrombus formation by minimizing blood flow disturbance, high shear stress, and stagnation. The pivot configuration includes a recess, preferably in the housing, that has a profile which promotes smooth blood flow.

10 Claims, 6 Drawing Sheets

MECHANICAL HEART VALVE PROSTHESIS

FIELD OF THE INVENTION

The present invention generally relates to mechanical heart valve prostheses. More specifically, the present invention relates to mechanical heart valve prostheses having improved pivot designs.

BACKGROUND OF THE INVENTION

Prosthetic valves are utilized to replace malformed, damaged, diseased or otherwise malfunctioning valves in body passageways, such as heart valves, including the tricuspid valve, the mitral valve, the aortic valve and the pulmonary valve. Such prosthetic heart valves are typically implanted into the heart either by open chest surgery which requires a sternotomy or by minimally invasive surgery which requires a thoracotomy between adjacent ribs.

Heart valve prostheses may be divided into two groups, namely, tissue valves and mechanical valves. Typically, prosthetic tissue valves are harvested from a suitable animal heart, usually a porcine heart, prepared according to known methods, and may be mounted to a stent to facilitate implantation. Tissue valves prepared from pericardial tissue are also known in the art. Mechanical valves, by contrast, utilize synthetic materials to form a valve having a ball, a disc, a pair of leaflets (bileaflet), or a plurality of leaflets to regulate blood flow therethrough.

A mechanical heart valve prosthesis is optimally designed to perform the same functions as a healthy native valve. In particular, a mechanical heart valve is designed to regulate blood flow into and out of the heart chambers. Mechanical heart valves permit blood flow in only one direction and are actuated between an open position and a closed position by the changing hemodynamic conditions of the heart—i.e., by changes in blood flow and pressure caused by the pumping action of the heart.

Ideally, a mechanical heart valve prosthesis imposes no more resistance to blood flow than a healthy native heart valve. However, mechanical valves typically have somewhat less efficient flow and may be more thrombogenic than healthy native valves. The inefficient flow may be caused by limitations associated with the design, such as the pivots, the profile or shape of the leaflets, and movement of the leaflets relative to the pivots. Such design limitations may cause disturbed flow such as excessive turbulence, high shear stress, flow separation, and recirculation to occur across the valve, which may increase the thrombogenic risk of the valve. Improvements in flow efficiency and thrombogenic resistance are desirable to more closely simulate a healthy native valve.

A particularly successful mechanical heart valve prosthesis design utilizes leaflets that are disposed in and pivotally attached to an annular housing. For each leaflet, there are two pivots that typically include a protrusion formed on the leaflet which is rotatably disposed in a recess formed in the housing. Such pivot assemblies may be susceptible to some degree of thrombus formation because blood flow may become disturbed and/or stagnant as it passes through the pivot.

To address the issue of thrombus formation, a standard practice among treating physicians is to provide anticoagulant therapy. The administration of anticoagulants reduces coagulation protein function and platelet aggregation which are precursors to thrombus formation. However, such anticoagulant therapy may lead to internal bleeding, which is undesirable. Therefore, it is desirable to reduce the probability of thrombus formation in another manner.

SUMMARY OF THE INVENTION

The present invention provides several pivot designs for mechanical heart valve prostheses that inherently reduce the probability of thrombus formation by minimizing the stagnation and disturbance of blood flow through the pivot assembly. The pivot designs of the present invention provide a depression or recess, preferably in the housing, that have a profile adapted to promote less disturbed and/or less stagnant blood flow.

In one aspect, the pivot depression or recess may have a smooth continuous surface free of surface protrusions or stopping walls to minimize flow disturbance and stagnation. A separate pair of stop protrusions for each leaflet may be disposed on the lumen surface of the housing to maintain the leaflets in the open and/or closed position if desired. Another embodiment includes providing curved profiles to the leaflets and valve body to reduce flow disturbances.

In one aspect, a pivot recess may have a central radius of curvature, an upstream radius of curvature and a downstream radius of curvature, wherein the radius of curvature varies therebetween in order to reduce blood flow disturbance and/or stagnation. In one aspect, a pivot recess may have a convex surface in addition to a concave surface in order to reduce the size of the recess and still minimize flow disturbance and/or stagnation.

DETAILED DESCRIPTION OF THE PREFERRED EMBODIMENTS

The following detailed description of the invention should be read with reference to the drawings, which are not necessarily to scale, in which similar elements are numbered the same. The detailed description and drawings depict selected preferred embodiments and are not intended to limit the scope of the invention.

Figure 1A:
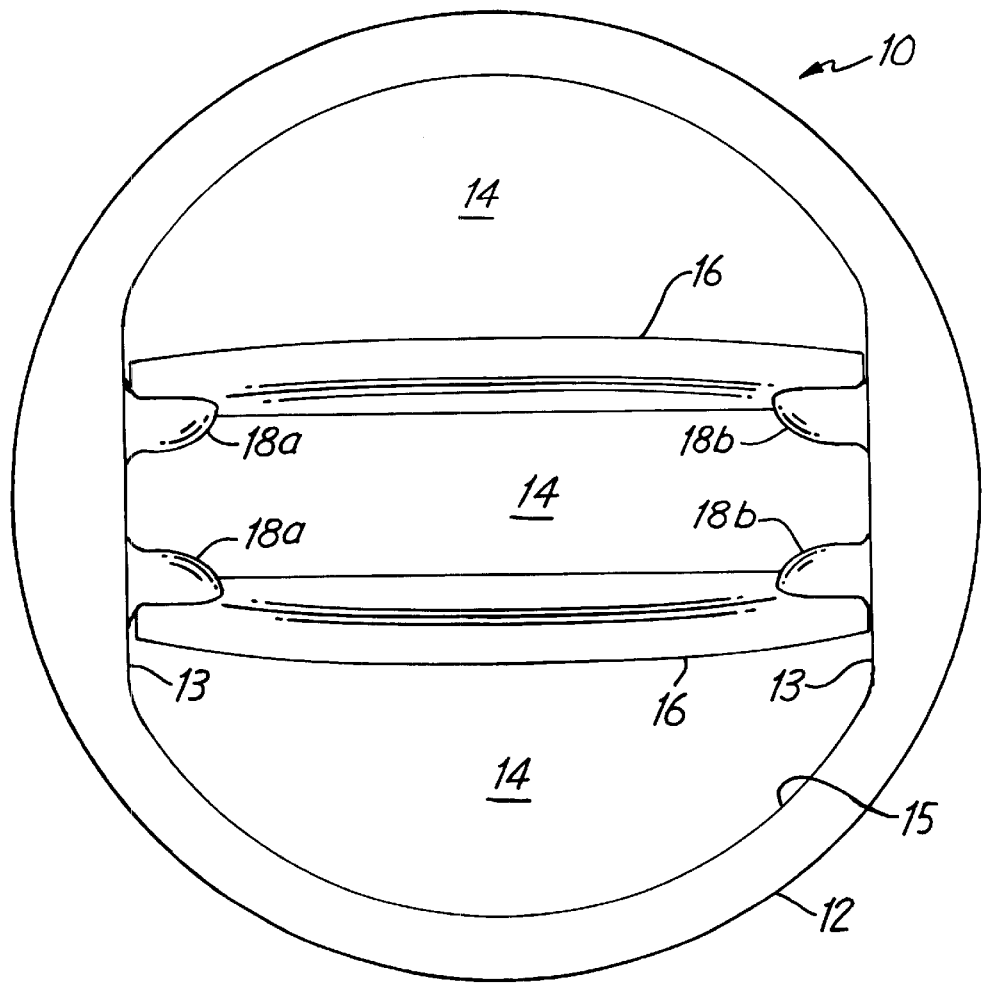
FIG. 1A is a perspective view of a mechanical heart valve prosthesis in accordance with an embodiment of the present invention.

FIG. 1A is an illustration of a mechanical heart valve prosthesis 10 in accordance with one embodiment of the present invention. Heart valve prosthesis 10 includes a generally circular orifice body or housing 12 having a generally circular orifice or opening 14 extending therethrough. Although illustrated as a circular housing 12 and circular opening 14, those skilled in the art will recognize that many suitable shapes may be employed, depending on the anatomical geometry of the implant site.

Heart valve prosthesis 10 further includes a pair of occluders or leaflets 16 disposed in the opening 14. Leaflets 16 are pivotally mounted to the valve housing 12 and are movable between an open position and a closed position. When the leaflets 16 are in their closed position, the opening 14 is substantially closed. Conversely, when the leaflets 16 are in their open position, the opening 14 is substantially open thus allowing the passage of blood therethrough. Although two leaflets 16 are illustrated in FIG. 1A, those skilled in the art will recognize that any suitable number of leaflets may be utilized.

The heart valve prosthesis 10 further includes protrusion stops 18 extending from the lumen surface 15 of the housing 12. Stops 18 are preferably on the downstream edge of housing 12 or a suitable location on flat portion 13. Protrusion stops 18 serve to limit the motion of the leaflets 16 as the leaflets 16 move to their open position. As such, protrusion stops 18 may be characterized as open stops. Although the heart valve prosthesis 10 as illustrated in FIG. 1A includes only open stops 18, it is contemplated that closing stops (not shown) may also be utilized. Such closing. stops may be used to limit the motion of the leaflets 16 as they rotate to their closed positions. Furthermore, the number of protrusion stops 18 may be varied, depending on the number of leaflets. Preferably, a, pair of protrusion stops 18a, 18b are used for each leaflet 16.

As shown in FIG. 1A, it may be seen that all of the components of the heart valve prosthesis 10 preferably have generously rounded edges. For example, inside corners and edges of the housing have generous fillets. Further, the housing, leaflets, protrusions, recesses and any other elements are preferably rounded and do not include sharp corners. By providing generously rounded leading and/or trailing edges, and generous fillets on the inside corners and edges of the heart valve features, blood flowing past the heart valve prosthesis 10 through the opening 14 is less likely to experience flow disturbance, stagnation or high shear stress along the edges of the heart valve prosthesis 10. Thus, the risk of thrombus formation is decreased.

Figure 1B:
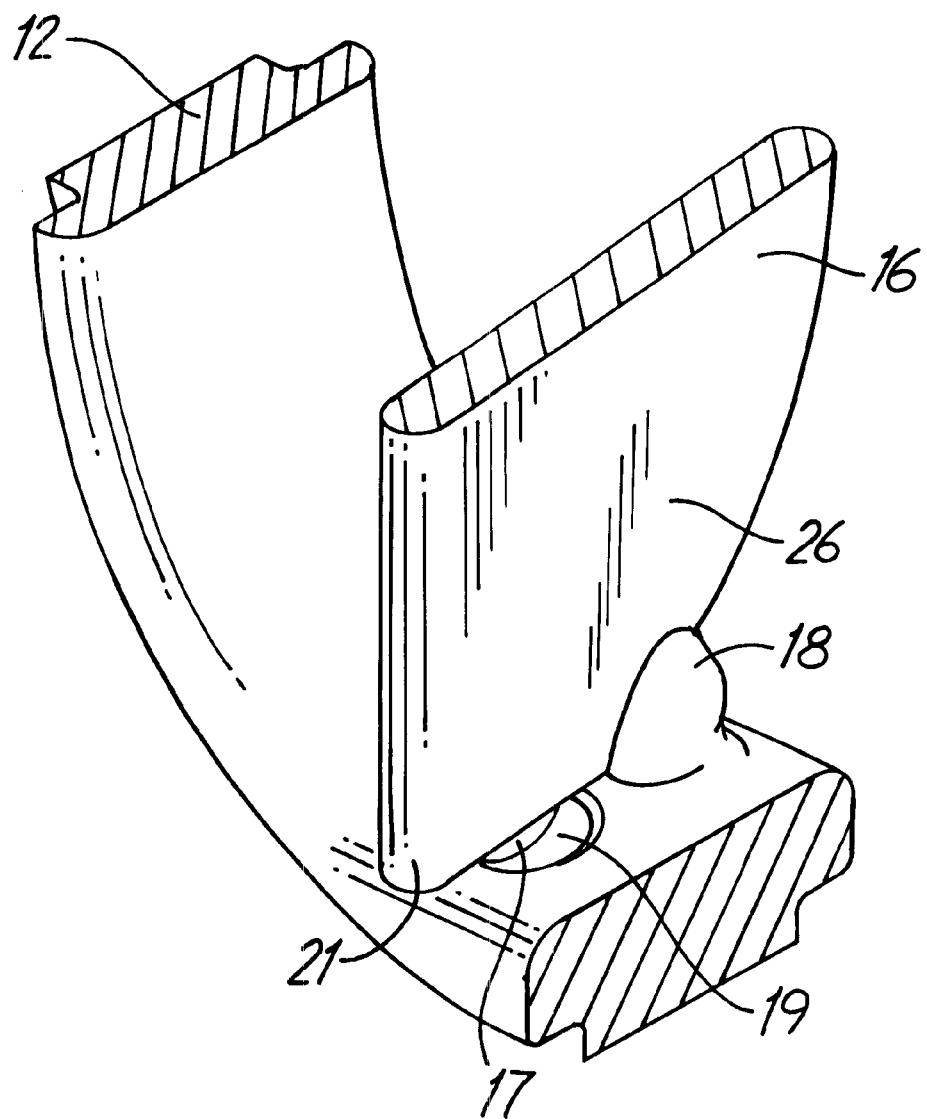
FIG. 1B is a detailed perspective view of the protrusion stops and pivot recesses of the mechanical heart valve prosthesis illustrated in FIG. 1A.

Preferably, the edges of the component (i.e., housing, leaflets or protrusions) of the heart valve prosthesis 10 have a radius of curvature approximately equal to one half the thickness of the respective part. For example, the leaflets 16 may have a leading edge 21 radius of curvature equal to approximately one-half the thickness of the leaflet 16 as shown in FIG. 1B. Similarly, the heart valve housing 12 may have a leading edge radius of curvature equal to approximately one-half the thickness of the housing 12. The radius of curvature of the leading edge along the flat portion 13 of the housing 12 is approximately equal to the leading edge radius of curvature along the remainder of the housing 12. Protrusion stops 18 preferably have a leading edge radius of curvature approximately equal to one half of their thickness. The leading and trailing edges of each component of the heart valve prosthesis 10 may be generously rounded in order to maintain smooth flow of blood across the various components.

In an embodiment, the leading edge of a heart. valve component may approximate the shape of a Rankine curve. An example of a Rankine curve is the locus of points defined. by the equation $R=a/\cos(\phi/2)$. A chord is defined as the axis of a component in a direction parallel to the forward blood flow direction. In the equation, R is a line from a fixed point on a chord of the component (occluder or housing ring) to the locus of points defining or approximating the leading edge in section, $\phi$ is an angle from the chord to R, which preferably ranges from $-180°$ to $180°$, with $\phi=0$ along the chord, directed upstream, and a is a constant related to the component thickness. Preferably $a=t/4$, where t is a component thickness downstream of the leading edge. In one embodiment, the generously rounded leading edge of a stop protrusion, in section, approximates a Rankine curve. In one embodiment, the axis of the component leading. edge, in section, is aligned to the direction of blood flow at peak systole (for an aortic valve) or peak diastole (for a mitral valve) even in embodiments where the occluder (leaflet) axis is at an angle to the flow.

The Reynolds number (a nondimensional hydrodynamic parameter) for blood flow at peak systole for an aortic valve, or peak diastole for a mitral valve, can be as large as 4000 or more. Rankine curve leading edges, aligned with their axis parallel to oncoming flow, may be the least disruptive to flow at Reynolds numbers of 4000 or more.

Therefore, for these embodiments of components of the invention, blood flow at leading edges will be minimally disturbed, fluid shear stresses will be reduced, and platelets will be less likely to be activated. Therefore, the potential for platelet aggregation and thrombus near the leading edges will be minimized.

Heart valve housing 12 may be made of pyrolytic carbon or other suitable material and may be made by conventional techniques. Protrusion stops 18 are preferably integral with the housing 12 or may be made separately and secured to the inside surface of the housing 12 by a suitable adhesive, snap or friction fit, or other attachment mechanism. The overall dimensions of the heart valve prosthesis 10 and its associated components may be selected based on the particular anatomical geometry in which the prosthesis 1.0 will be implanted.

FIG. 1B is a detailed view of the open protrusion stops 18 and pivot recesses 19 of the heart valve prosthesis 10 as illustrated in FIG. 1A. As stated previously, the leaflets 16 are pivotally mounted to the inside surface of the housing 12 by means of a pivot assembly which includes a pivot recess 19 and an occluder or leaflet protrusion 17 extending from the outside edge of the leaflet 16. Because protrusion stops 18 are provided, it is not necessary to include a stop mechanism inside the pivot recess 19. As such, pivot recess 19 is free of protrusions and has a smooth continuous surface of revolution to reduce flow disturbance and possible flow stagnation. The protrusion stops 18 engage a body portion 26 of the leaflets 16, rather than the leaflet protrusions 17 extending into the pivot recesses 19. Therefore, the leaflet protrusions are less susceptible to wear and damage caused by friction and impact forces. Another advantage is that structural loading (stresses) on leaflet protrusions 17 is greatly reduced. Although spherical pivot depressions or recesses 19 are illustrated in FIG. 1B, other pivot depression profiles may be utilized as described hereinafter. An advantage of a pivot recess 19 without stops is that the valve may have an opening angle of greater than 84°. A pivot mechanism which reduces the amount of wear and damage imparted to leaflet protrusions 17 and/or pivot recesses 19 facilitates the use of special coatings on these surfaces, which would otherwise not be possible since the coating may be worn away in prior art valves. The coating may consist of materials which prevent thrombosis or infection, such as heparin, drug-delivery coatings or otherwise.

Each leaflet 16 may utilize one, two or more separate protrusion stops 18a, 18b to limit the rotational movement of the leaflet 16 in its open position. As stated previously, although no closing stops are necessary because the edges of the leaflets contact each other and the housing 12, it is contemplated that protrusion closing stops may also be utilized.

Figure 1C:
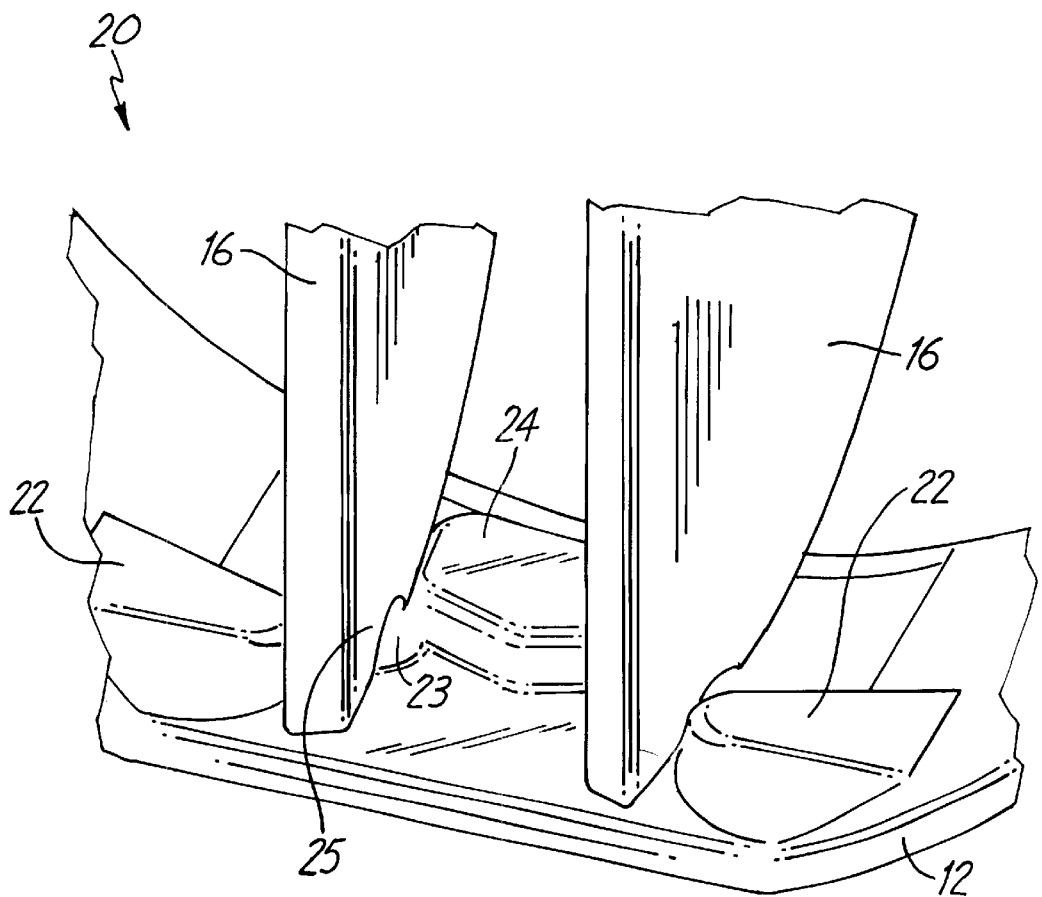
FIG. 1C is a perspective view of a prior art mechanical heart valve prosthesis.

FIG. 1C is a detailed view of a prior art mechanical heart valve prosthesis 20. Except as described herein with reference to FIG. 1C, all other aspects of the heart valve prosthesis 20 are the same as described previously with reference to mechanical heart valve prosthesis 10. In this particular heart valve, the pivot assembly is composed of spherical protrusions 23 extending outwardly from the flat portions 13, which mate with depressions 25 in the leaflets. The opened and closed positions of the leaflets 16 are controlled by opening and closing stops 22 and 24. Opening and closing stop 24 is shared by the two leaflets.

Figure 1D:
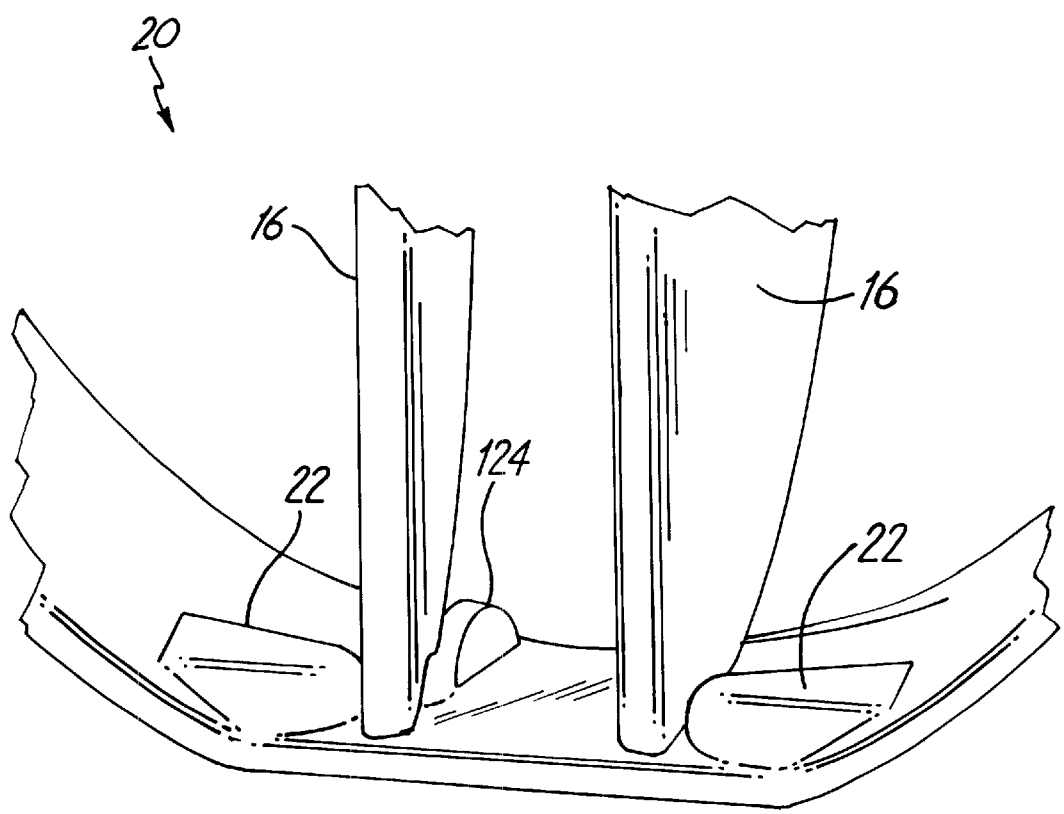
FIG. 1D is a perspective view of a mechanical heart valve prosthesis in accordance with another embodiment of the present invention.

In the present invention, shown in FIG. 1D, stop 24 would be replaced by two separate opening stops 124. This is accomplished by either forming a groove in stop 24 (such as by removing material) or replacing stop 24 with stops 124a,b. This allows the blood to pass relatively undisturbed through the passageway formed by the groove in stop 24 or between the stops 124. In the prior art-valve in FIG. 1C, blood encounters stop 24 and is diverted (laterally left or right) such that it is forced through the gap formed between the leaflet 16 and stop 24 as well as the gap formed between the leaflet 16 and the valve housing 12. Blood flowing through small gaps may have two implications. The first is that when the blood is forced to squeeze through a small gap, the blood encounters high shear stresses, which may damage the blood cells and activate blood clotting factors thereby leading to thrombosis and/or anemia. Secondly, after passing through the small gap, blood enters the relatively stagnant area behind stops 22 and the leaflet 16. Some of the blood will be diverted up and over stop 24 causing a large wake behind it. This may also cause flow stagnation and increase the risk of thrombosis. Stagnant blood is a risk factor for blood clot formation: Preferably, stop protrusions 124 or grooved stop 24 have a generously rounded profile to reduce flow disturbance and/or stagnation areas.

By providing separate protrusion stops 124 for each of the leaflets 16, as opposed to a single protrusion stop 24 that is shared between the leaflets 16, blood is permitted to flow between the protrusion stops 124, thereby reducing flow disturbance and stagnation. By reducing flow disturbance and stagnation, the probability of thrombus formation is reduced and anticoagulant therapy may be reduced.

FIGS. 2–5 illustrate various pivot depression or recess profiles for use in a mechanical heart valve prosthesis such as prosthesis 10 and 20 illustrated in FIGS. 1A, 1B and 1D. For purposes of clarity, only the pivot recess is illustrated in FIGS. 2–5, but those skilled in the art will readily recognize that all other conventional components may be utilized to form a complete and functional heart valve prosthesis.

Figure 2:
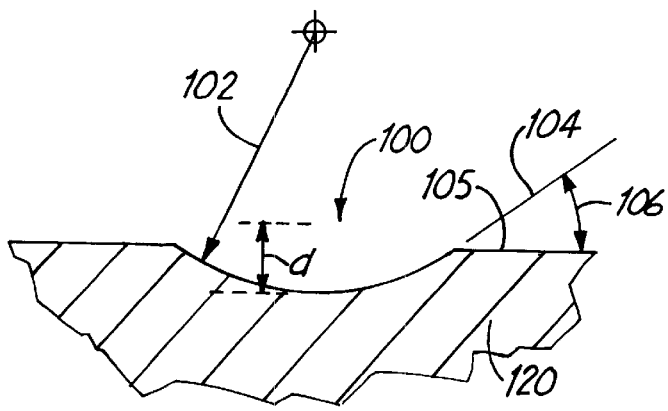
FIG. 2 is a cross sectional view of a prior art pivot depression.

FIG. 2 illustrates a prior art pivot recess or depression 100 in the valve housing 120. Pivot recess 100 has a spherical profile with a radius of curvature indicated by arrow 102. Each pivot depression 100, 30, 40 and 50 illustrated in FIGS. 2, 3, 4 and 5, respectively, have the same depth d for comparative purposes only. The intersection between the inside surface of the recess 100 and the inside surface of the housing 120 defines an angle 106 between tangent line 104 and tangent line 105. A large tangent angle 106 may tend to cause blood flow separation and stagnation within the recess 100.

In studies with non-anticoagulated animals, platelet aggregates have been observed to accumulate in the recess 100 despite the wiping motion of the leaflet protrusion. These platelet aggregates were observed to accumulate in regions of the recess 100 where flow separation, recirculation or stagnation may occur. These flow disturbances appear to be associated with abrupt changes in the geometry of the recess 100, such as the intersection between the inside surface of the recess 100 and the inside surface of the housing 120.

Although anticoagulant therapy tends to reduce platelet aggregation and thereby reduce thrombus formation, anticoagulant therapy may increase the probability of internal bleeding.

Figure 3:
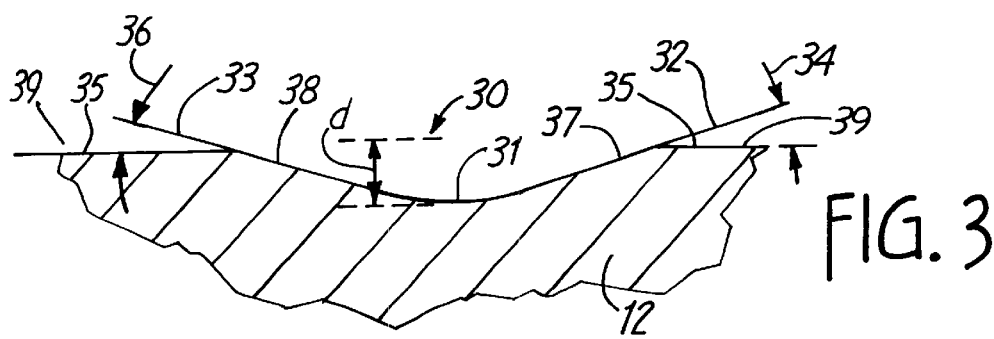
FIG. 3 is a cross sectional view of a pivot depression in accordance with one embodiment of the present invention.

FIG. 3 is a cross-sectional view of pivot depression 30 in accordance with one embodiment of the present invention. Pivot depression 30 has a concave central portion 31 and a slightly curved or linear outer portion 37,38 defined by tangent lines 32 and 33, respectively. The upstream portion 37 of recess 30 is defined by tangent line 32 and the downstream portion 38 of recess 30 is defined by tangent line 33. Tangent line 32 intersects the inside or lumen surface 39 of the valve housing 12 at tangent line 35 to define upstream angle 34. similarly, tangent line 33 intersects the inside or lumen surface 39 of valve housing 12 at tangent line 35 to define downstream angle 36. The upstream angle 34 and the downstream angle 36 are each less than the angle 106 of the prior art pivot recess 100. The smaller angles 34 and 36 provide a smooth transition between the recess 30 and the lumen surface 39 of the valve housing 12 to reduce flow disturbance and/or stagnation. The upstream angle 34 may be less than 30° and is preferably less than 8°. The downstream angle 36 may be less than 45° and is preferably less than 8°.

Figure 4:
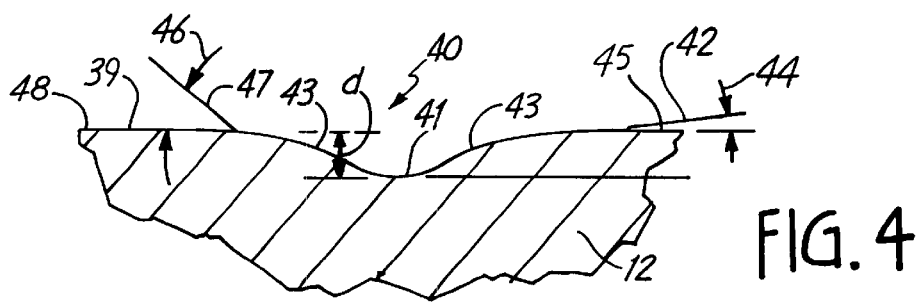
FIG. 4 is a cross sectional view of a pivot depression in accordance with another embodiment of the present invention.

FIG. 4 is a cross-sectional view of a pivot recess 40 in accordance with another embodiment of the present invention. Recess 40 includes a concave central portion 41 and a convex outer portion 43. A tangent line 42 extending from the outer convex portion 43 of the recess 40 intersects the inside or lumen surface 39 of the valve housing 12 at tangent line 45 to define upstream angle 44. Recess 40 also has a downstream angle 46 defined by tangent lines 47,48 that may be the same as, larger than or smaller than upstream angle 44. The upstream angle 44 of recess 40 illustrated in FIG. 4 is substantially smaller than the upstream angle 106 of the prior art recess 100 illustrated in FIG. 2. The relatively small upstream angle 44 reduces flow disturbance and/or stagnation in the recess 40. The downstream angle 46 may be less than 45° and is preferably less than 8°. The upstream angle 44 may be less than 30° and is preferably less than 8°.

The upstream curve (for blood flow entry during forward flow) and downstream curve (for blood flow exit during forward flow) of the recess may have different radii of curvature or profiles in one or more embodiments. In such embodiments, the profile of the recess is not a figure of revolution. In embodiments with upstream and downstream curves of identical radius of curvature or profile, the recess profile conforms to a figure of revolution.

As stated previously, the recesses 100, 30, 40 and 50 illustrated in FIGS. 2, 3, 4 and 5, respectively have a depth d that is the same for comparative purposes only. The recess forms an intersection with the inside or lumen surface 39 of the valve housing 12. In planview, in one embodiment, the intersection is of generally continuous and circular form. In another embodiment, a stop wall is included within the recess and the intersection includes arcuate segments of a generally circular form. The largest diameter of the generally circular form of the intersection is the "intersection diameter." As compared to recess 100 illustrated in FIG. 2, recess 30 illustrated in FIG. 3 has a larger intersection diameter for the same recess depth. By contrast, recess 40 illustrated in FIG. 4 has a relatively small intersection diameter for the same recess depth while maintaining a relatively small upstream angle 44 and downstream angle 46. By providing a recess 40 having a concave central portion 41 and a convex outer portion 43, a relatively small upstream angle 44 and downstream angle 46 may be achieved without increasing the intersection diameter of the recess 40, for the same recess depth. This is of benefit due to the limitation of space on the lumen surface, especially in small valves.

An advantage of the invention is that entry (upstream) and exit (downstream) angles may each or both be minimized, while maintaining a secure capture mechanism for the leaflet. The capture mechanism security is enhanced by the relatively large recess depth for capture. Prior art spherical-section recesses may allow for a small angle, but only for quite shallow recess depths. The prior art recess would consist of a small segment of a sphere. Such prior-art shallow recess depths would not provide highly secure capture of the leaflet. Loss of capture of the occluder (leaflet) is extremely deleterious to the patient and requires emergency surgery to preserve the patient's life.

For invention embodiments including a stop within the pivot recess, the upstream (blood flow entry) and/or downstream (exit) angles are each allowed to be a minimum by the invention, and secure capture of the occluder (leaflet) is maintained. Thus the invention advantageously provides the minimum angles that are important for minimization of flow disturbances and potential consequent platelet activation, aggregation and thrombus formation. In contrast, prior-art spherical-section recesses with stops are unable to accomplish all these advantages simultaneously.

Figure 5:
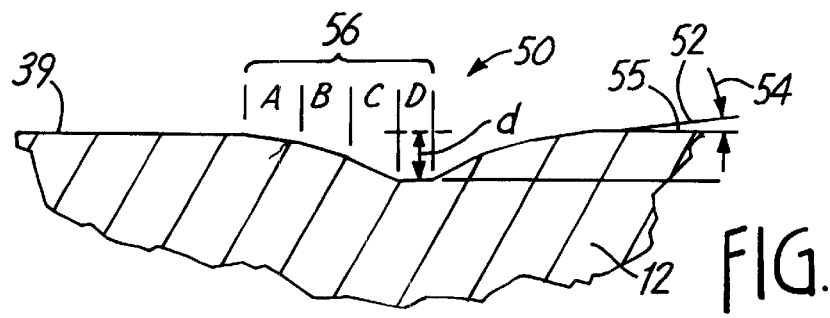
FIG. 5 is a cross sectional view of a pivot depression in accordance with yet another embodiment of the present invention.

FIG. 5 is a cross-sectional view of a pivot depression 50 in accordance with yet another embodiment of the present invention. Pivot depression 50 is similar to pivot depression.40 by virtue of the concave central portion and the convex outer portion. However, the inside surface of recess 50 differs from the inside surface of recess 40 in that the inside surface of recess 50 is divided into a series of inclined surfaces or facets 56. For purposes of clarity, only the downstream inclines 56 are illustrated in FIG. 5.

Each incline or facet 56A, B, C and D forms an angle with the inside surface of the housing 12. For example, the outermost upstream facet has a tangent line 52 which intersects the inside surface of orifice housing 12 defined by tangent line 55 to form upstream angle 54. It is contemplated that any number of inclines or facets 56 may be utilized. As the number of inclines or facets 56 increases, the inside surface of recess 50 approximates the inside surface of recess 40. Each upstream angle may be less than 30° and preferably less than about 8°. Each downstream angle may be less than 45° and preferably less than about 8°. The lengths of both the upstream and downstream facets 56 may be less than about 0.004 inches (0.1 mm).

Figure 6:
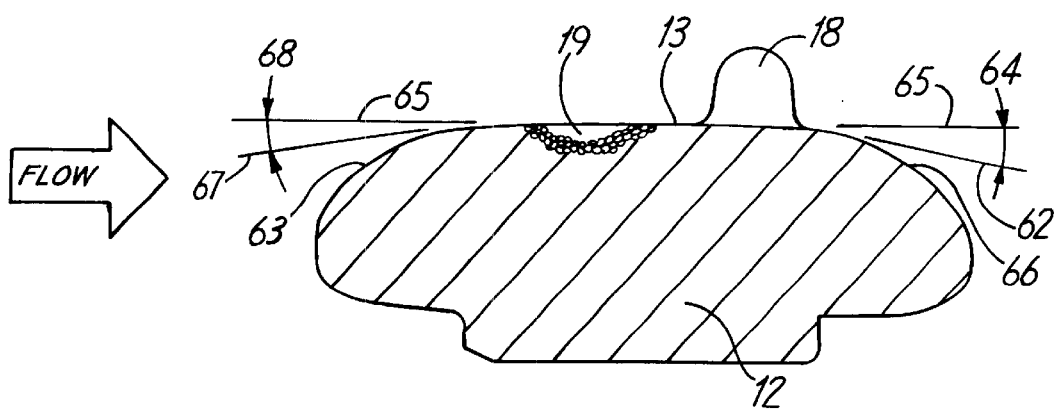
FIG. 6 is a cross sectional view of an orifice housing with an upstream fairing and a downstream fairing in accordance with one embodiment of the present invention.

Further, in one embodiment, as illustrated in FIG. 1B, housing 12 does not include the fairing or "thumb nail" depressions in flat portion 13 as found in prior art configurations. Most prior art valves have a fairing (or ramp) on the leading and/or more commonly on the trailing edge of the housing. For the most part, this fairing(s) is in the area of the pivot where the housing is thicker to accommodate the pivot mechanism. The purpose of the leading edge fairing is to direct the flow over this thickened area in a smooth, undisturbed manner. The purpose of the trailing edge fairing is to expand the flow from this thickened area to the housing downstream edge in a smooth, undisturbed manner. Computational fluid dynamics studies of flow over these fairings, has shown that the fairing geometry is important to achieve the smooth flow desired. The geometry described with respect to FIGS. 3, 4 and 5 may be applied to a fairing design to ensure smooth flow over this region. One embodiment of the present invention is shown in FIG. 6. FIG. 6 is a section view of an orifice housing 12 with an upstream fairing 63 and a downstream fairing 66. The intersection of upstream fairing 63 with the flat portion 13 of housing 12 is defined by tangent line 65 and tangent line 67. The tangent lines 65 and 67 form an upstream angle 68. The intersection of downstream fairing 66 with flat portion 13 of housing 12 is defined by tangent line 65 and tangent line 62. The tangent lines 65 and 62 form a downstream angle 64. Each angle 68 and 64 is less than 20° and preferably less than 8°. The profile of each fairing 63 and 66 may be any of the convex, linear, or slightly concave profiles described in FIGS. 3–5.

There are numerous advantages of the present invention over the prior art. One advantage of the present invention is that it provides a smoother flow through the valve. The invention overcomes problematic geometries in prior art valves. In contrast, the pivot area in prior art valves is problematic as the flow encounters protrusions, walls, and depressions disturbing the flow. The leaflet and housing edges in prior art valves are also problems, as the fluid has to divert around them.

One embodiment of the invention has spherical pivot depressions (or any other recess shape) that have no stopping walls within the depression or recess that force the flow. to abruptly change course. In the current invention, the blood freely flows into the depression and directly out of it, thus reducing the flow disturbance, fluid shear, and/or stagnation, which may lead to thrombosis.

As no stopping walls are required in the depression, opening stopping walls in the depression may be replaced by stopping protrusions outside of the depression to control the range of motion of the leaflet. These stopping protrusions can take the form of generously rounded protrusions. In the prior art, these stopping protrusions take the form of a large protrusion that is shared by the two leaflets. This is not desirable since the flow hitting this large protrusion either has to go around it causing the fluid to be forced under the leaflet or over the large protrusion causing a large wake behind it. In one embodiment, the valve is improved by either putting a deep groove in the large protrusion or replacing the large protrusion by two smaller generously rounded protrusions as shown in FIGS. 1A and 1B. In this design, blood is free to move undisturbed between the protrusions rather than having to go around or over them.

Another advantage of not having stopping walls in the depression is that the leaflet ear will not hit the walls. This reduces friction and wear on the leaflet ear. With no friction and wear present, the use of coatings in the pivot depressions and/or on the leaflet ear to prevent thrombosis is possible. Such coatings may include elemental silver and/or drugs, among others which prevent or break up blood clots (thrombus) or reduce the risk of infection. Coatings may be used to release heparin or urokinase to prevent or break up clots. It may be possible that with the use of these coatings, anti-coagulation therapy may be reduced or eliminated. In addition, this reduced friction and wear allows the use of softer material, such as an elastomer or polymer in this area (ear and/or housing) which may reduce leakage when the valve is closed, as well as reduces valve opening and closing impact noise.

Another advantage of the invention is that the valve fairing can be optimized to produce smooth flow using the profiles described in FIGS. 3–6. Prior art fairing shapes produce disturbed and/or separated flows.

Another aspect of the invention is to have no downstream fairing (thumbnail). This is advantageous because the blood will not be disturbed or separated due to the fairing, until exiting the valve housing where it is of less consequence.

Yet another advantage of this invention is the generously rounded edges of the leaflets and housing. Prior art leaflets have sharp corners that cause the flow to separate near the leading edge of the leaflet, which causes high fluid shear stress and possibly thrombus formation. This is particularly evident when the leaflet leading edge is at an angle of attack to the flow. Incorporating generously rounded edges on the housing or leaflets allows the flow to remain attached to the leaflet or housing longer. Thus, flow disturbance is greatly reduced. This will greatly reduce the tendency of the blood to clot.

In one embodiment, the beneficial upstream features of the pivot recesses in FIGS. 3–5 are applied to a fairing joining the leading edge of the housing to the lumen surface of the housing. This housing leading edge fairing is of convex curvature or a nearly flat ramp or very slightly concave. The angle of the fairing with the housing lumen surface is small, less than 20 degrees and preferably less than 8 degrees.

In one embodiment, the beneficial downstream features of the pivot recesses in FIGS. 3–5 are applied to a fairing joining the trailing edge of the housing to the lumen surface of the housing. This housing trailing edge fairing is of convex curvature or a nearly flat ramp or very slightly concave. The angle of the fairing with the housing lumen surface is small, less than 20 degrees and preferably less than 8 degrees.

Although the present invention has been described with reference to preferred embodiments, workers skilled in the art will recognize that changes may be made in form and detail without departing from the spirit and scope of the invention.

What is claimed is:

1. A mechanical heart valve prosthesis, comprising:

an orifice body having a lumen surface and an orifice for the passage of blood therethrough, the orifice body including at least two opposed pivot depressions disposed on the lumen surface, the pivot depressions having smoothly curved central portions and substantially linear outer portions which form upstream and downstream angles with a tangent line of the lumen surface, the depressions configured to reduce disturbed flow and stagnation;

at least one occluder disposed in the orifice and pivotally attached to the orifice body, the occluder movable about an axis of rotation between an open position and a closed position such that the orifice is substantially open when the occluder is in its open position and the orifice is substantially closed when the occluder is in its closed position, the occluder further having two opposed occluder protrusions rotatably disposed in the pivot depressions; and an open protrusion stop for the occluder, the stop protrusion disposed on the lumen surface of the orifice body.

2. A mechanical heart valve prosthesis as in claim 1 wherein two occluders are disposed in the orifice and pivotally attached to the orifice body.

3. A mechanical heart valve prosthesis as in claim 1 wherein a plurality of occluders are disposed in the orifice and pivotally attached to the orifice body.

4. The mechanical heart valve prosthesis as in claim 1 wherein the upstream angle is less than 30°.

5. The mechanical heart valve prosthesis claim 1 wherein the upstream angle is less than 8°.

6. The mechanical heart valve prosthesis as in claim 1 wherein the downstream angle is less than 45°.

7. The mechanical heart valve prosthesis as in claim 1 wherein the downstream angle is less than 8°.

8. The mechanical heart valve prosthesis as in claim 1 wherein the upstream angle is less than 300 and the downstream angle is less than 45°.

9. The mechanical heart valve prosthesis as in claim 1 wherein the upstream angle is less than 8° and the downstream angle is less than 8°.

10. The mechanical heart valve prosthesis as in claim 1 wherein the upstream and downstream angles are different.

* * * * *

UNITED STATES PATENT AND TRADEMARK OFFICE
CERTIFICATE OF CORRECTION

PATENT NO. : 6,395,025 B1  
DATED : May 28, 2002  
INVENTOR(S) : Fordenbacher et al.

It is certified that error appears in the above-identified patent and that said Letters Patent is hereby corrected as shown below:

Column 10,  
Line 32, after "prosthesis" insert -- as in --.  
Line 39, delete "300" and replace it with -- 30 --.

Signed and Sealed this

Twenty-ninth Day of October, 2002

Attest:

JAMES E. ROGAN  
Attesting Officer     Director of the United States Patent and Trademark Office